United States Patent [19]
Tobin

[11] Patent Number: 5,997,566
[45] Date of Patent: Dec. 7, 1999

[54] CRICOTHYROTOMY FORCEPS

[76] Inventor: Joshua Tobin, 55 Forbes Rd., Westwood, Mass. 02090

[21] Appl. No.: 09/114,976

[22] Filed: Jul. 14, 1998

[51] Int. Cl.$^6$ .................................................. A61B 17/28
[52] U.S. Cl. ............................................................ 606/205
[58] Field of Search ................................... 606/205, 206, 606/207, 208, 209, 210, 148, 139, 144, 145

[56] References Cited

U.S. PATENT DOCUMENTS

| | | | |
|---|---|---|---|
| 5,618,305 | 4/1997 | Lolagne | 606/205 |
| 5,746,748 | 5/1998 | Steinberg et al. | 606/205 |
| 5,746,757 | 5/1998 | McGuire | 606/205 |
| 5,797,919 | 8/1998 | Brinson | 606/205 |

*Primary Examiner*—Michael Buiz
*Assistant Examiner*—(Jackie)Tan-Uyen T. Ho
*Attorney, Agent, or Firm*—Joshua M. Tobin

[57] ABSTRACT

A cricothyrotomy forceps for inserting an endotracheal tube through an incision in the crico-thyroid membrane particularly designed for use by a paramedic in the field and having a pair of coupling plates extending perpendicular to the jaws of the forceps on only to one side of the plane defined by the handles and having a wound introduction margin designed to facilitate the entry of an endotracheal tube through the incision into the trachea. The forceps may be packaged in a kit with a tube of a length designed for a cricothyrotomy.

19 Claims, 8 Drawing Sheets

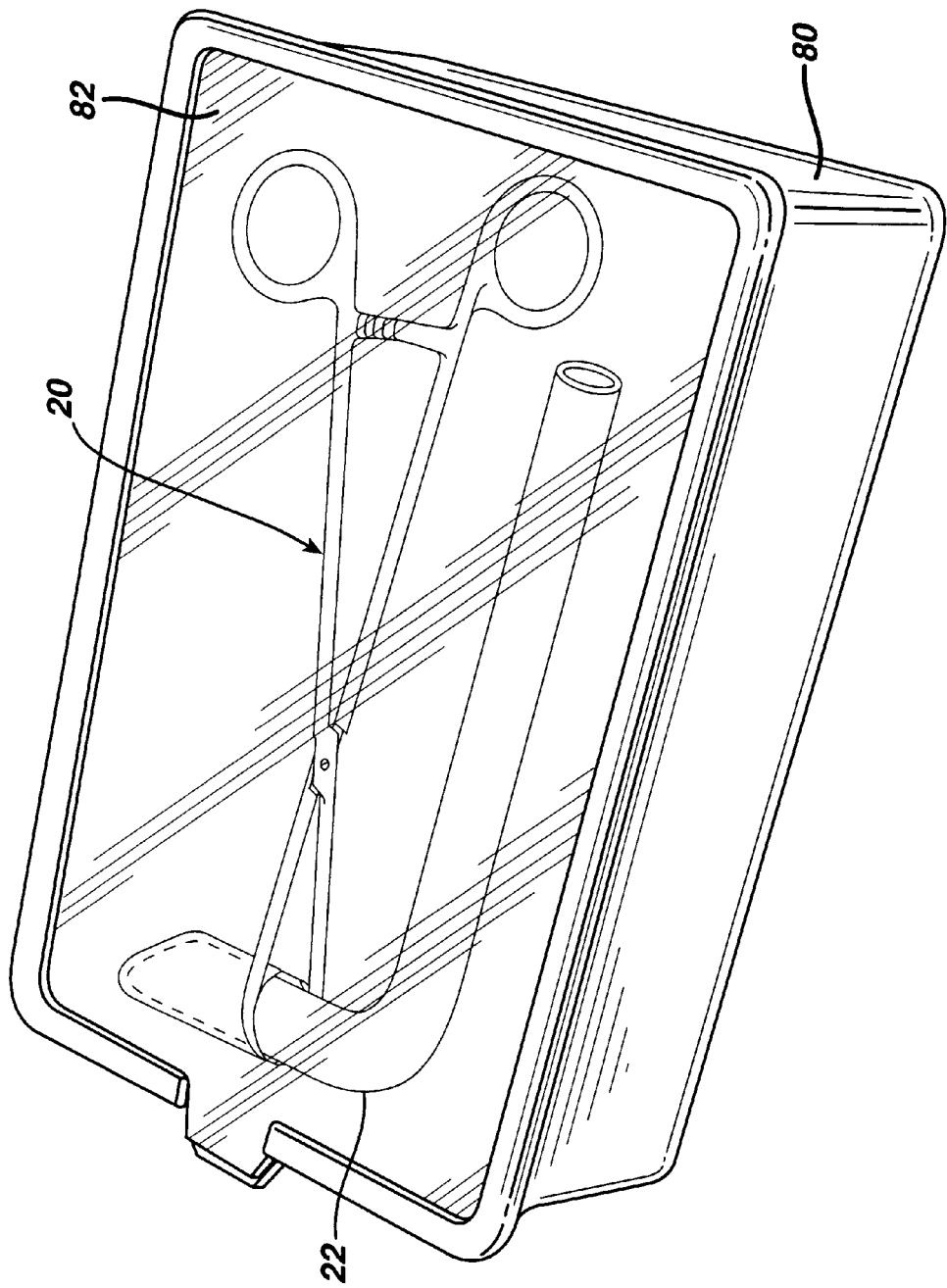

CRICOTHYROTOMY FORCEPS

BACKGROUND OF THE INVENTION

The present invention relates to a forceps specially designed for inserting an endotracheal tube into the trachea of a patient through the crico-thyroid membrane.

It is important during emergency care to keep the patient's airway open. In fact, emergency care providers are trained to place attention on the Airway first, before Breathing and Circulation (the so-called ABC's of emergency care). The airway is easily obstructed. Anything from the patient's own tongue, blood, vomitus or small bits of food can occlude the airway, interrupting the flow of air into and out of the lungs. Failure to provide adequate oxygen to the lungs, and ultimately to the brain, can result in hypoxia, which can rapidly progress to anoxia and death. The most common technique in the emergency setting for securing the airway is to place an endotracheal tube into the trachea of the patient through the mouth. In some instances, the endotracheal tube can be inserted into the trachea through the nasal passages via the nasal-tracheal route. Sometimes oral or nasal introduction of the endotracheal tube is either not possible or is contra-indicated. For example, if the patient's jaw is clenched shut, one cannot use the oral-tracheal route. Blood flowing from the nose could be an indication of a basilar skull fracture, thus contra-indicating the nasal-tracheal route. At the scene of an accident, paramedics sometimes find patients with clenched jaws from a closed head injury or with blood flowing from the nose from a skull fracture. Inadequate respiration must be resolved in those instances by a surgical intervention through the crico-thyroid membrane.

As shown in FIG. 1, the crico-thyroid membrane (16) is a transverse oval-shaped membrane located below the thyroid cartilage (12) and above the cricoid cartilage (14) in the throat just below the prominence commonly known as the Adam's Apple (15).

The thyroid (derived from the Greek word for "shield") is the largest cartilage in the larynx and is shown in FIG. 2. It consists of two lateral walls (17, 19) united at an acute angle in front forming a vertical projection in the middle line which is prominence above and called the Adam's Apple (15). Each side is quadrilateral in form. The upper border (21) of the thyroid cartilage (12) is sinuously curved and is concave on the posterior part (23). The lower border of the thyroid cartilage (12) is nearly straight in front. This lower border of the thyroid cartilage (12) is connected to the cricoid cartilage (14) in and near the median line by the middle portion of the crico-thyroid membrane (16) and, on each side, by the crico-thyroid muscle (not shown). The cricoid cartilage (14) (derived from the Greek work for "ring" because it resembles a signet ring) is smaller, but thicker and stronger than thyroid cartilage (12) and forms the lower and back part of the cavity of the larynx. It consists of two parts: a quadrate portion (24) situated to the rear and a narrow ring anterior portion (23) or arch about ¼ or ⅕ the depth of the posterior part, situated in front, thus, the appearance of a signet ring. The quadrate portion (24) rapidly narrows at the sides of the cartilage into the anterior portion (23). The anterior portion (23) is narrow and convex and affords attachment externally in front and at the sides of the crico-thyroid muscle (not shown). The lower border of the cricoid cartilage (14) is horizontal and connected to the upper ring of the trachea (18) by fibrous membrane. The upper border of cricoid cartilage (14) is directed obliquely upward and backward owing to the greater depth of the posterior surface. It gives attachment in front through the middle portion of the crico-thyroid membrane (16), at the sides to the lateral portion of the same membrane. The crico-thyroid membrane (16), thus, extends between the lower margin of the thyroid cartilage (12) and the upper margin of the cricoid cartilage (14). It is convex, concealed on each side by the crico-thyroid muscle, but subcutaneous in the middle line. It can accommodate endotracheal access through the tough cartilage below the vocal cords and at the entry way to the trachea (18).

In the hospital setting, surgeons use advanced tools to perform a surgical cricothyrotomy or they use the more difficult and technically advanced tracheotomy procedure. At the scene of an emergency, like a motor vehicle accident, paramedics do not have at their disposal the equipment that is available in the hospital setting. The only tool available to the paramedic is a scalpel to make the incision laterally across the crico-thyroid membrane. The fifth digit is used for blunt dissection prior to inspection of the endotracheal tube (22).

An endotracheal tube (22) is a curved, bendable plastic tube of a prescribed internal diameter varying usually from 3 to 9.5 mm and with a bias cut distal end (25). The tube (22) is introduced into the trachea (18) through a 10 mm incision (67) in the crico-thyroid membrane (16). The incision is made across the crico-thyroid membrane (16) transverse to the long axis of the neck of the patient. It can be very difficult to advance the tube (22) down trachea (18) since it is being introduced at a 90-degree angle through the incision with only a millimeter or two to spare. Paramedics frequently find that they have to make a larger incision in order to turn the endotracheal tube down the longitudinal axis of the trachea (18) or the paramedic must slowly advance the tube (22) into the trachea (18) by using the fifth digit to bend the distal end of the tube (22) in order to navigate the 90-degree angle, thus, wasting valuable time and executing an extremely difficult digital maneuver. When one considers the confusion that can exist at an emergency scene, one can easily see that it would be extremely helpful to have a device specially designed for use in the field to perform a surgical cricothyrotomy more easily without resorting to the surgeon's tray full of instruments.

Standard endotracheal tubes designed for oral entry are longer than is necessary for a crico-thyroid membrane entry. When they are used in a crico-thyrotomy, the proximal end of the tube sticks out too far from the incision and can get in the way or even be hit by the attending personnel causing additional damage to adjacent structures.

The description of the anatomy was taken from Gray's Anatomy 1977, Crown Publishers, Inc., Library of Congress Catalog No. 76-52804, pp. 955–965.

SUMMARY OF THE INVENTION

It would be useful to have a cricothyrotomy forceps to assist in placing an endotracheal tube through an incision in the crico-thyroid membrane into the trachea. A standard forceps is used with first and second arms usually made of stainless steel hinged together to form handle portion proximal of the hinge and a pair of jaws distally of the hinge so that as the handles are opened and closed, the jaws correspondingly open and close. A special coupling plate is attached to the distal end of each jaw and extends in a plane away from and preferably perpendicular to the plane defined by the two arms of the forceps. In the preferred embodiment, the coupling plates are generally rectangular and have a distal margin and a proximal margin extending away from the jaws which are connected together by a wound insertion margin, which in the preferred embodiment, defines an acute angle with the distal margin. Alternatively, the wound introduction margin can form an acute angle with the proximal margin or can be rounded in a direction concave to the plane of the handles. In a further alternative, the two coupling plates can extend from the jaws at an angle and converge toward the incision introduction margin to assist in opening the incision as the coupling plates are inserted.

The opposing surfaces of the two coupling plates may be curved concavely with respect to one another to generally conform to the outside surface of the endotracheal tube which they are designed to hold. The opposing surfaces of the coupling plates may include a high friction area which can be accomplished by a coating of natural or synthetic rubber or by providing a mechanically roughened surface.

Alternatively, the whole forceps could be made of a sufficiently strong plastic or combination of plastic and metal.

A standard locking mechanism could be used to allow the quick one-hand locking of the two arms of the handle portion together so that after the endotracheal tube was secured between the coupling plates, it could be securely held there by locking the forceps handles together.

The special forceps of the present invention is used to insert the distal end of the endotracheal tube by first making a transverse incision across the cricoid-thyroid membrane with a scalpel and grasping an endotracheal tube between the opposed coupling plates with the distal end of the tube withdrawn somewhat proximately of the incision introduction margin of the coupling plates. The user, then, locks the forceps together and places the forceps adjacent the neck of the patient with one of the plates lying against the patient's skin adjacent the incision and with the forceps' handles extending generally parallel to the longitudinal axis of the neck. The forceps handles are then rotated parallel to the longitudinal axis of the neck to introduce the distal end of the endotracheal tube into the incision. The incision introduction margin of the coupling plates are tapered so as to assist in spreading apart the edges of the incision through the crico-thyroid membrane. This tapering can be from the distal to the proximal margin of the plates or the plates themselves may taper toward each other. Thus, the endotracheal tube is introduced into the trachea with its distal end extending perpendicular to the axis of the of the trachea. The handles which now lie parallel to the patient's neck are, then, raised away from the neck causing the coupling plates inside the wound to rotate with the endotracheal tube, thus, positioning the endotracheal tube parallel to the longitudinal axis of the trachea. The forceps is, then, unlocked and removed from the wound while holding the tube in place with the hand. The endotracheal tube may, then, be easily advanced down the trachea a sufficient distance. The trachea is, then, secured in the usual way and the airway is established.

It may also be convenient to provide the cricothyrotomy forceps of the present invention in a single use version possibly made of plastic in a sealed and possibly sterile kit with or without an accompanying tube of an appropriate length for use in a cricothyrotomy.

These and other features of the present invention will be more fully described in conjunction with the following description of the preferred embodiment and the following drawings.

DETAILED DESCRIPTION OF THE PREFERRED EMBODIMENT

Figure 1:
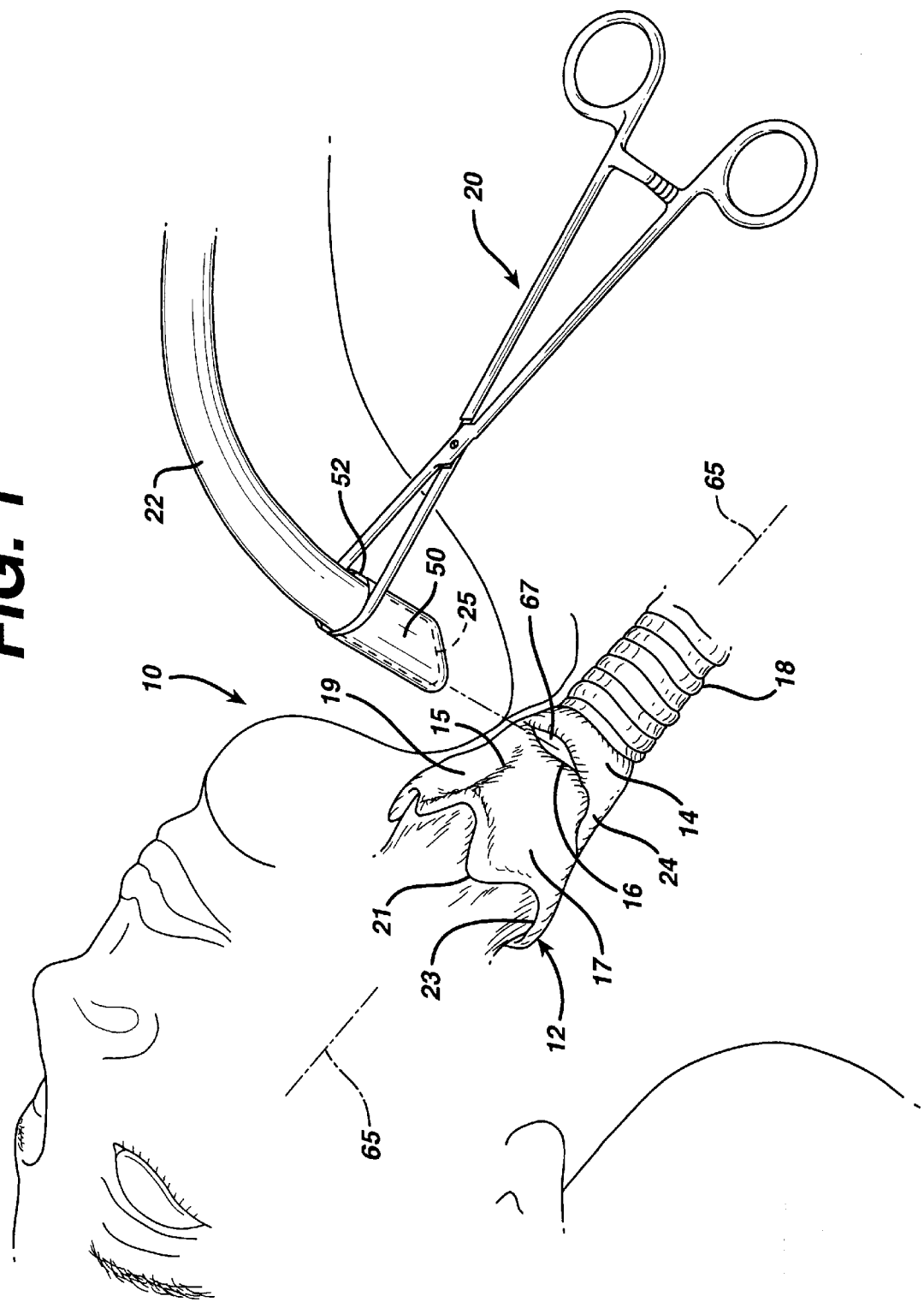
FIG. 1 shows a frontal view of the patient's neck partly in section showing schematically the crico-thyroid membrane and its surrounding thyroid and cricoid cartilage at the top of the trachea.

Referring now to FIG. 1, there is shown a front view of a human subject's head, neck and upper chest cut away to illustrate schematically the thyroid cartilage (12), the cricoid cartilage (14) and the crico-thyroid membrane (16) disposed between the lower margin of thyroid cartilage (12) the upper margin of the cricoid cartilage (14). Also shown is the forceps (20) of the present invention holding an endotracheal tube (22) ready for insertion. The forceps (20) of the present invention will first be described followed by a description of its use to insert an endotracheal tube (22) through an incision (67) in the crico-thyroid membrane (16).

Figure 4:
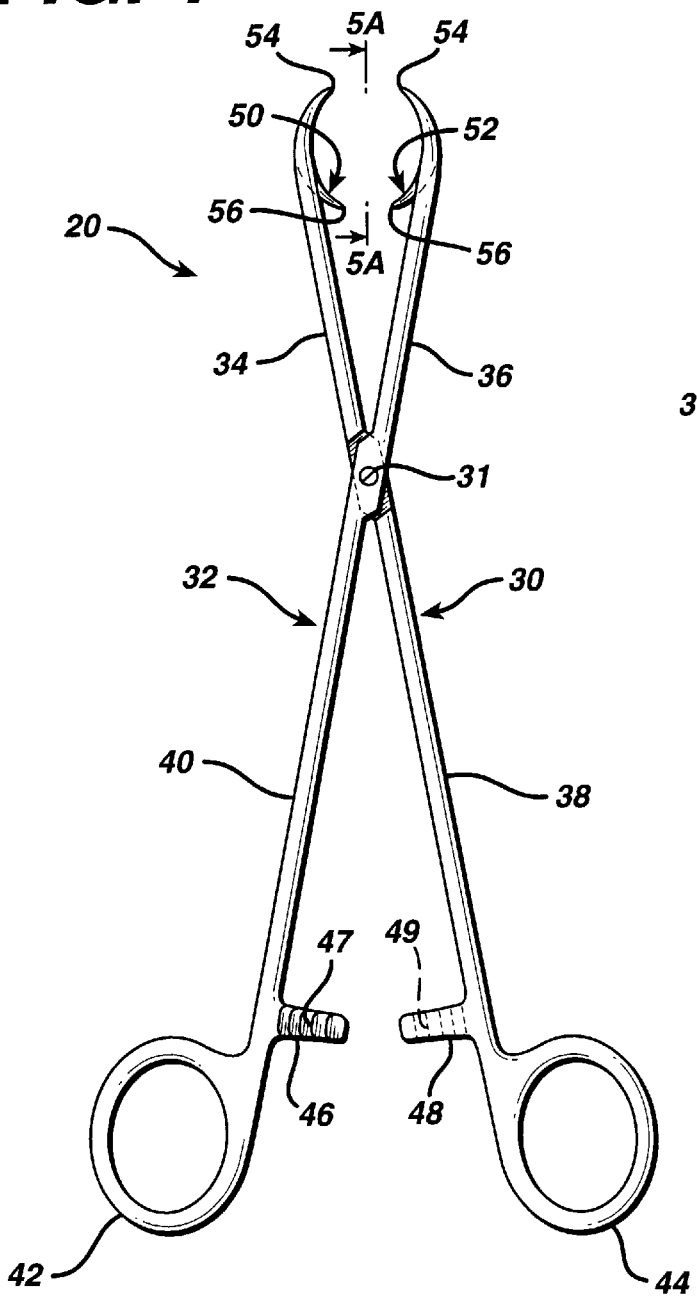
FIG. 4 shows a plan view of the forceps of the present invention.
Figure 4A:
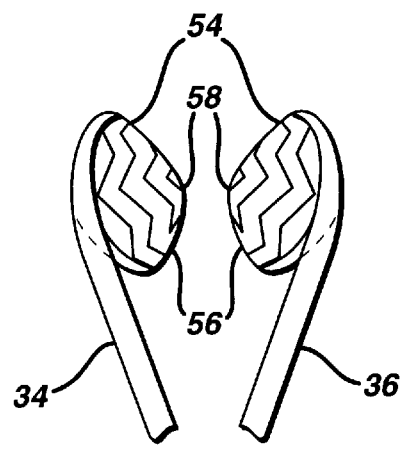
FIG. 4a shows a modified forceps of the present invention.

Referring now to FIG. 4, forceps (20) includes first arm (30) and second arm (32) connected by hinge (31) which may be any conventional hinge like a screwed lap joint or a box lock. Jaws (34) and (36) project distally from hinge (31) and handle sections (40) and (38) project proximally from hinge (31). Each handle (38) and (40) preferably includes a finger loop (42, 44). Forceps (20) is equipped with standard locking mechanism which includes locking arms (46) and (48) extending from handle sections (40) and (38) toward each other. Opposing surfaces of the locking arms (46) and (48) include interfitting ratchet surfaces (47) and (49) which will automatically lock together and hold handles (38) and (40) and hence jaws (34) and (36) at a desired spacing while jaws (34) and (36) are holding an endotracheal tube (22). In the preferred embodiment, arms (30) and (32) are made of straight material so as to define a plane when they are connected together at hinge (31). The arms and hence jaws and handles are preferably made of stainless steel like a standard forceps, but can alternatively be made of a suitably strong plastic better adapted for a single use disposable instrument convenient for a paramedic to use in the field.

Figure 5:
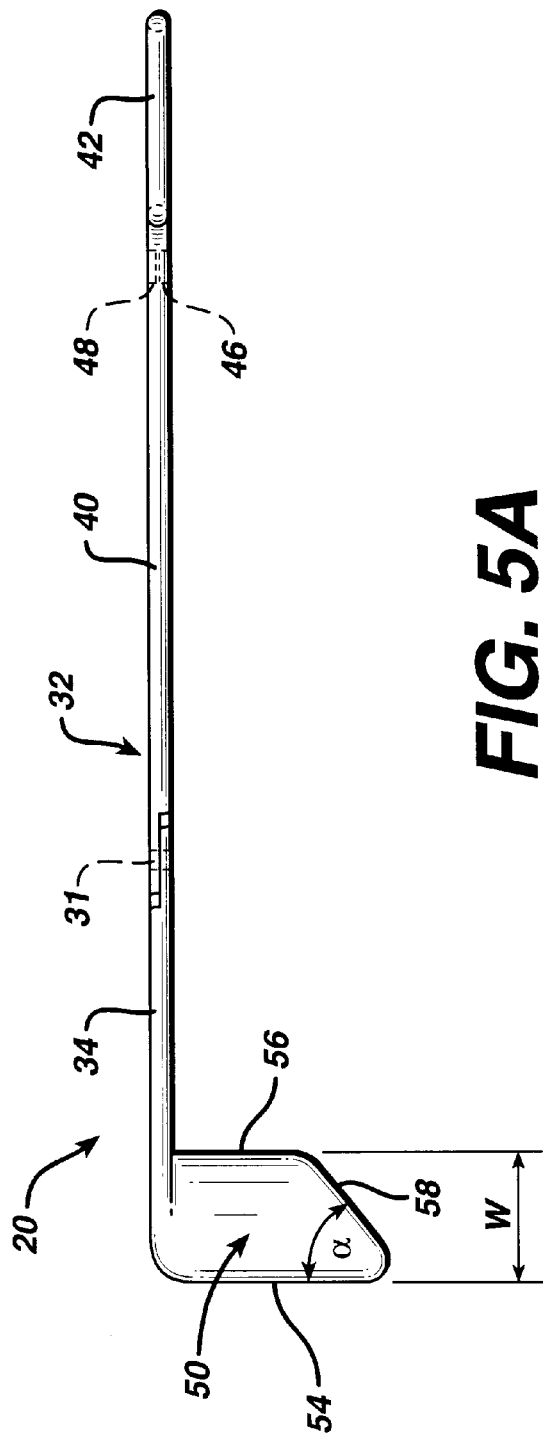
FIG. 5 shows a side view of the forceps of the present invention.
Figure 5A:
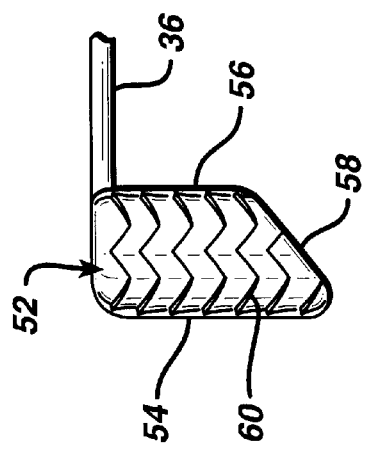
FIG. 5A shows a surface of one portion of the forceps of the present invention.

Coupling plates (50) and (52) extend away from the plane defined by handles (38) and (40). Referring now to FIGS. 1 and 5, each coupling plate (50) and (52) is a generally rectangular in cross-section and has a distal margin (54) and a proximal margin (56). Incision introduction margin (58) is tapered so as to form an acute angle ($\alpha$) with distal margin (54). The tapered incision introduction margin (58) makes it easier to insert each coupling plate (50, 52) through the incision (67), as will be explained in more detail below. All of the edges of the generally rectangular coupling plates (50) and (52) are rounded to avoid damaging any of the delicate tissue involved in a cricothyrotomy. In the preferred embodiment, as can be seen best in FIG. 4, the distal and proximal margins (54) and (56) of each coupling plate (50) and (52) are curved inwardly toward the opposite jaw so as to form a concave surface for better holding the curved perimeter of an endotracheal tube (22). The particular extent of the curvature of the concavity of the opposing surfaces of coupling plates (50) and (52) is not critical but should be selected so that it can comfortably hold a variety of endotracheal tubes commonly used in the field.

The confronting surfaces of the coupling plates (50) and (52) may include a high friction surface like rough surface (60). Alternatively, the confronting surfaces of coupling plates (50) and (52) can be coated with rubber or some high friction plastic material.

Preferably the overall length of the forceps of the present invention is 15 to 20 cm and the hinge is placed about 5 cm from the distal end of the forceps (20). The locking arms are approximately 3 cm from the handle end of the forceps.

The coupling interface provided by coupling plates (50) and (52) holds the endotracheal tube securely. Each plate extends two or three centimeters transversed to the plane of arms (30) and (32) at an angle of approximately 90 degrees and in the same plane as the axis of a hinge (31). Each coupling plate (50) and (52) has a width (w) of approximately 1.5 cm (see FIG. 5). The taper at the incision introduction margin (58) of each coupling plate (50) and (52) forms an angle of about 30 to 45 degrees to be axis of the hinge.

Figure 6A:
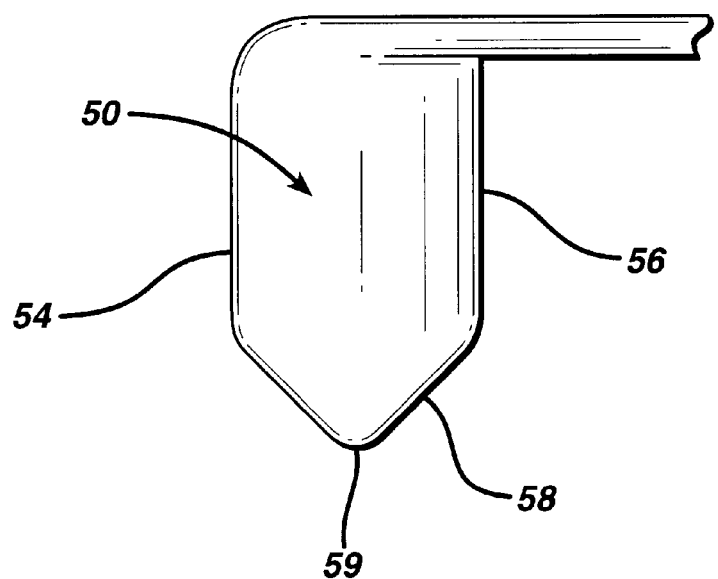
FIGS. 6A and 6B show alternative embodiments of the coupling plate portion of the present invention.
Figure 6B:
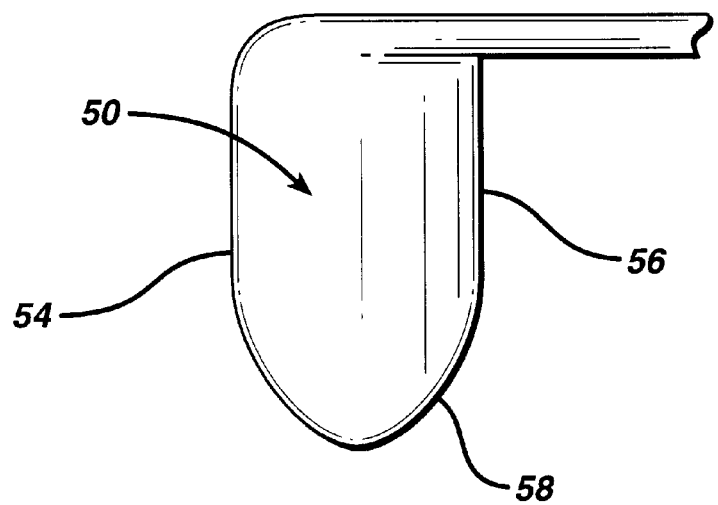

As shown in FIG. 6A and 6B, the incision introduction margin (58) of coupling plates (50) and (52) can form an obtuse angle with both the proximal margin (56) and the distal margin (54) coming together in a gentle rounded point (59) as shown in FIG. 6A or incision introduction margin (58) may be curved as shown in FIG. 6B.

In a further alternative (not shown), the incision introduction margin could form an acute angle with proximal margin (56) which is opposite of what is shown in FIG. 5.

Alternatively, coupling plates (50) and (52) may only be defined by marginal material extending around parameter of the plates so that the interior portion of each plate is open to provide easier visibility.

In a further alternative, the coupling plates (50) and (52) could be designed just as the one in FIG. 4, except that the two plates would taper toward each other as one advanced from jaws (34, 36) to incision introduction margins (58) so as to form a cup around the endotracheal tube to further assist in opening the incision during insertion procedure.

In use, endotracheal tube (22) is secured between coupling plate (50) and (52) with the aid of rough surfaces (60) and locking arms (46) and (48) are engaged so as to hold endotracheal tube (22) securely without having to maintain constant pressure on handles (38) and (40). The forceps holding the endotracheal tube (22) is laid on the patient's neck with the long axis of the forceps (20) parallel with the long axis (65) of the patient's neck.

A transverse incision (67) is made generally perpendicular to the long axis (65) of the patient's neck.

Figure 2:
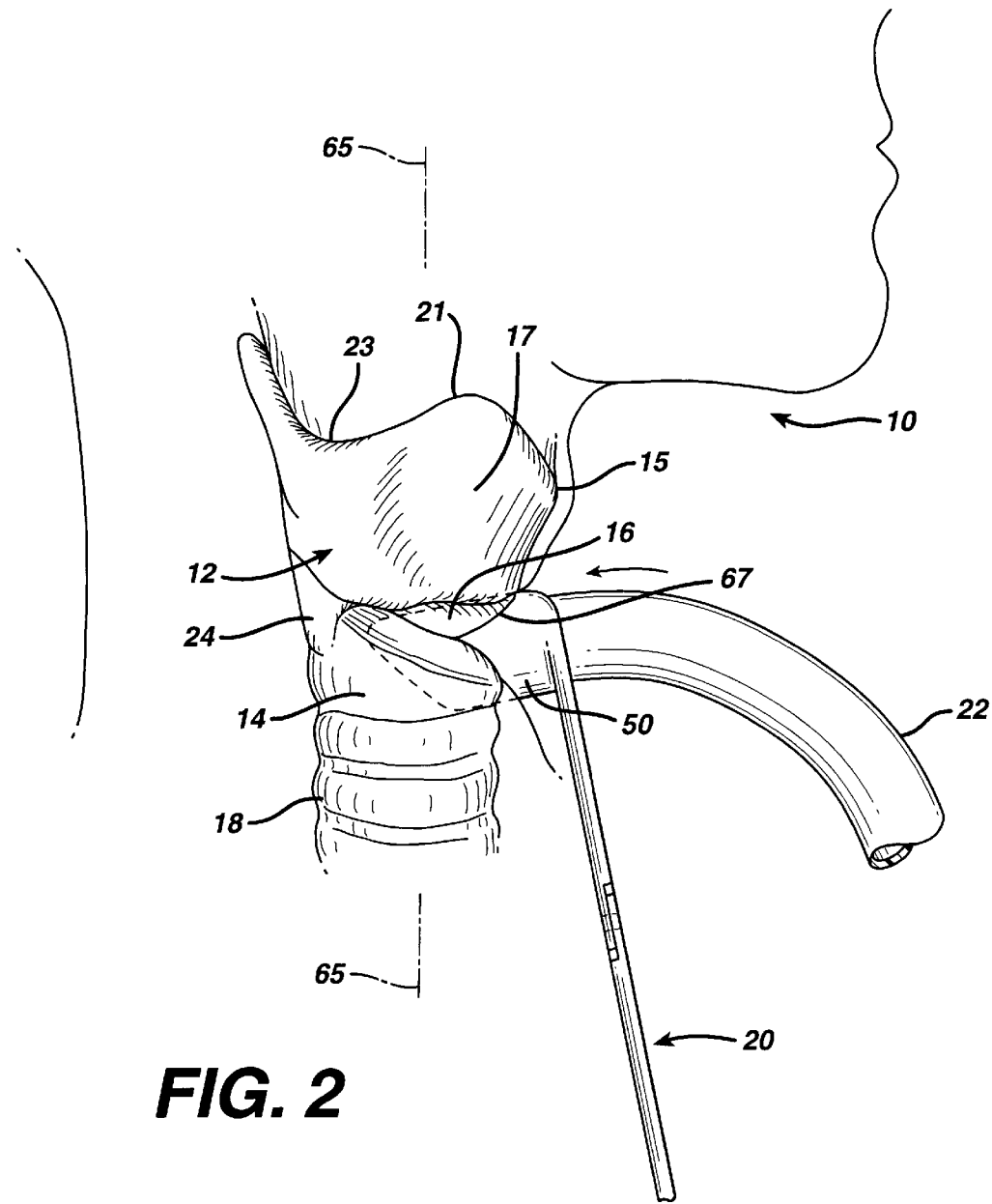
FIG. 2 shows a side view of the anatomy surrounding the crico-thyroid membrane with the endotracheal tube rotated through the incision and extending into the space just above the trachea perpendicular to the longitudinal axis of the trachea.
Figure 3:
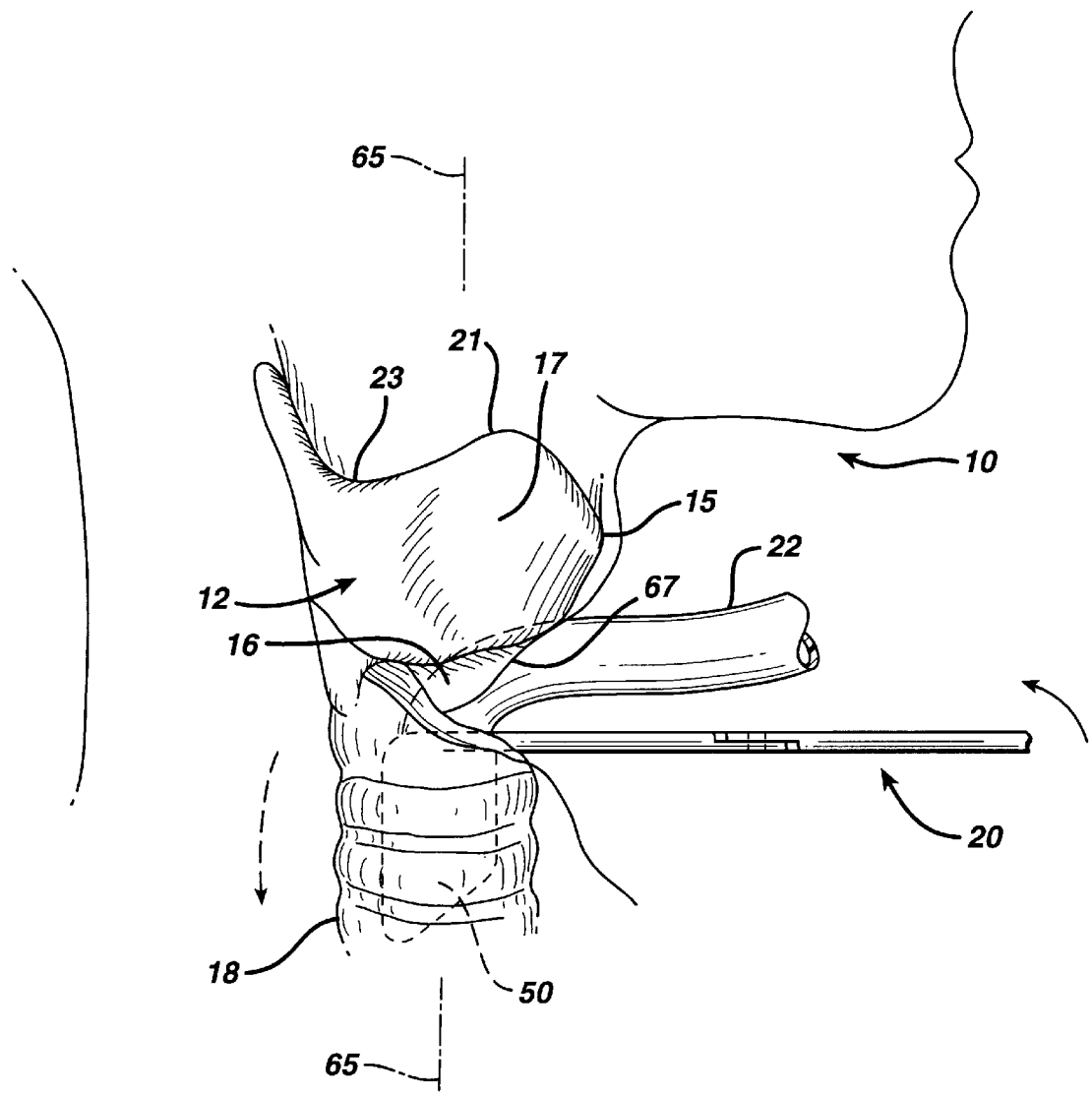
FIG. 3 shows the forceps of the present invention rotated perpendicular to the neck of the patient so as to move the endotracheal tube parallel to the longitudinal axis of the trachea.

The user, then, rotates the assembly 90 degrees such that the long axis of forceps (20) remains parallel with the long axis (65) of the patient's neck and coupling plates (50) and (52) introduced the endotracheal tube (22) into incision (67) as particularly shown in FIG. 2. Incision introduction margin (58) of coupling plates (50) and (52) helps spread the opposite sides of the incision to facilitate insertion of the endotracheal tube (22). Endotracheal tube (22) and coupling plates (50) and (52) are now inside the trachea (18), perpendicular to the long axis of the trachea which generally corresponds to long axis (65) of the patient's neck. The plane defined by handles (38) and (40) lies generally parallel to the patient's check. The user now rotates handles (38) and (40) upwardly away from the patient's chest such that handles (38) and (40) are aligned about 90 degrees to the long axis of the patient's neck and coupling plates (50) and (52) and endotracheal tube (22) lie parallel to the long axis of the trachea. Locking mechanism (46) and (48) is now disengaged. Forceps (20) is removed from the incision and endotracheal tube (22) remains in place. One may now easily advance endotracheal tube (22) into trachea (18). The endotracheal tube (18) is, then, secured in a conventional manner; for example, inflation of the distal cuff and taping of the tube to the patient's neck.

The present invention provides a tool that makes the field implementation by a paramedic of a cricothyrotomy much easier than it has been in the past.

Figure 7:
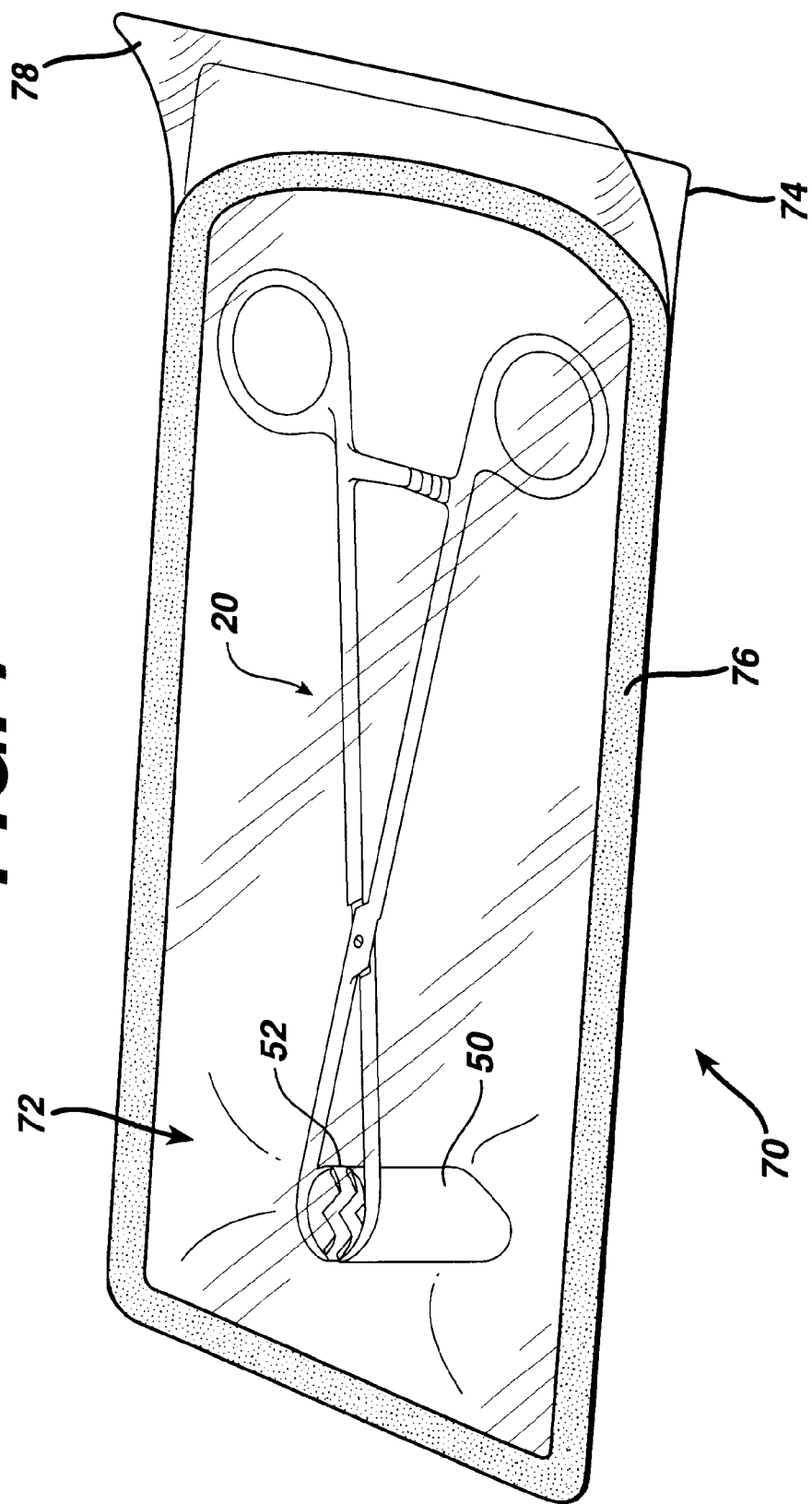
FIG. 7 shows a single use disposable forceps of the present invention in a sealed and possibly sterile kit; and, FIG. 8 shows the same forceps as FIG. 7 together with an appropriate length of tubing.

It may be convenient to supply the cricothyrotomy forceps (20) of the present invention in a sealed plastic contained like a pouch (70) shown in FIG. 7 with a top transparent plastic layer (72) sealed to a bottom transparent or opaque layer of plastic (74) sealed at their margins (76) in a suitable manner like gluing or ultrasonic welding. Unsealed flap (78) is left from layer (72) to act as a tab to assist in opening pouch (70).

As shown in FIG. 8, forceps (20) can be provided in a rigid tray (80) with a transparent cover (82) and a preloaded endotracheal tube (22). I recommend a 6.5 mm internal diameter endotracheal tube.

The present invention has been described in the context of its preferred embodiment. Certain changes in modifications to the preferred embodiment would occur to those skilled in this art. The scope of the invention is not intended to be limited except as set forth in the following claims.

I claim:

1. A cricothyrotomy forceps comprising:

first and second arms;

a hinge joining said first and second arms for pivotal motion;

said arms extending proximally from said hinge to form a forceps handle portion and extending distally from said hinge to form forceps jaws so that the opening and closing of the handle will correspondingly open and close the jaws;

a coupling plate attached to the distal end of each jaw and extending toward a coupling plate incision introduction margin away from one side of said arms;

each coupling plate having a distal margin and a proximal margin with respect to the hinge, an incision introduction margin connecting said plate distal margin and said plate proximal margin at a point most removed from the attachment point of the plate to its respective jaw;

said incision introduction margin being shaped to facilitate introduction into an incision.

2. The forceps of claim 1 wherein said distal margin and said incision introduction margin form an acute angle.

3. The forceps of claim 1 wherein said distal margin and said incision wound introduction margin form an obtuse angle.

4. The forceps of claim 1 wherein said incision introduction margin is curved concavely with respect to the attachment point of the respective plate to its jaw.

5. The forceps of claim 1 wherein each of said arms is straight so that the jaw portion and the handle portion operate in a single plane.

6. The forceps of claim 1 wherein the confronting surfaces of said coupling plates are concave with respect to each other to help grasp an endotracheal tube.

7. The forceps of claim 1 wherein the proximal margin of said plate is curved generally concavely with respect to the hinge to assist insertion into the wound.

8. The forceps of claim 1 wherein all of the edges of the margins of the plate are rounded.

9. The forceps of claim 1 wherein the opposing surfaces of the plates include a high friction surface.

10. The forceps of claim 9 wherein said high friction surface comprises rubber coating.

11. The forceps of claim 9 wherein said high friction surface comprises mechanical roughening of the opposing surfaces of the plates.

12. A method of inserting an endotracheal tube into the trachea comprising:

making an incision in the crico-thyroid membrane;

grasping an endotracheal tube between opposed plates affixed to the jaws of a forceps and extending away from one side of said arms;

placing said forceps adjacent the neck of the patient with one of the plates lying against and parallel to the skin adjacent the incision and with the forceps handles extending generally parallel to the longitudinal axis of the neck of the patient;

said plates having a distal margin and a proximal margin and an incision introduction margin;

rotating the forceps parallel to the longitudinal axis of the neck to insert the plates and correspondingly the distal end of the endotracheal tube through the incision in the crico-thyroid membrane with plates extending perpendicular to the longitudinal axis of the trachea;

raising the handles of the forceps away from the chest to rotate the plates approximately 90 degrees so they extend along the longitudinal axis of the neck into the trachea and correspondingly aligning the endotracheal tube along the distal axis of the trachea;

removing the forceps leaving the endotracheal tube in the trachea;

advancing the endotracheal tube into the trachea.

13. The forceps of claim 1 further including a handle lock so that when the finger rings are drawn together to hold an endotracheal tube between the jaws, the position of the two arms of the handle can be affixed together by the lock and then easily released when it is desired to move the handles apart.

14. The method of claim 12 wherein the incision is made perpendicular to the longitudinal axis of the neck across the crico-thyroid membrane.

15. The forceps of claim 1 wherein said coupling plates taper toward each other so that they are closer together at the incision introduction margin than at the point of attachment to the jaws.

16. A kit comprising the cricothyrotomy forceps of claim 1 sealed in a pouch, said pouch including:

a first sheet;

a second sheet sealed to the first sheet to form a pouch for said forceps; and, a pouch opening tab.

17. The kit of claim 16 further including an endotracheal tube disposed in said pouch.

18. The kit of claim 16 wherein at least one of said sheets is transparent.

19. The kit of claim 16 wherein at least one of said sheets is rigid.

* * * * *